United States Patent
Weiss et al.

(10) Patent No.: US 11,518,069 B2
(45) Date of Patent: Dec. 6, 2022

(54) METHOD OF FABRICATING A CASTING

(71) Applicant: THE UNIVERSITY OF SYDNEY, New South Wales (AU)

(72) Inventors: Anthony Steven Weiss, Sydney (AU); Richard Wang, Sydney (AU)

(73) Assignee: THE UNIVERSITY OF SYDNEY, New South Wales (AU)

( * ) Notice: Subject to any disclaimer, the term of this patent is extended or adjusted under 35 U.S.C. 154(b) by 0 days.

(21) Appl. No.: 17/056,782

(22) PCT Filed: May 21, 2019

(86) PCT No.: PCT/AU2019/050488
§ 371 (c)(1),
(2) Date: Nov. 19, 2020

(87) PCT Pub. No.: WO2019/222797
PCT Pub. Date: Nov. 28, 2019

(65) Prior Publication Data
US 2021/0122092 A1    Apr. 29, 2021

(30) Foreign Application Priority Data
May 21, 2018  (AU) .............................. 2018901766

(51) Int. Cl.
*B29C 41/00*  (2006.01)
*B22C 9/04*  (2006.01)
(Continued)

(52) U.S. Cl.
CPC ............. *B29C 41/003* (2013.01); *B22C 9/04* (2013.01); *B29C 41/36* (2013.01); *B29C 41/46* (2013.01);
(Continued)

(58) Field of Classification Search
CPC .......... B22C 9/04; B29C 39/003; B29C 41/36
See application file for complete search history.

(56) References Cited

U.S. PATENT DOCUMENTS

2004/0116997 A1   6/2004   Taylor et al.
2004/0258729 A1  12/2004   Czernuszka et al.
(Continued)

FOREIGN PATENT DOCUMENTS

CN     100490762 C     5/2009
CN     103317935 A     9/2013
(Continued)

OTHER PUBLICATIONS

First Office Action dated Nov. 15, 2021 received in Chinese Patent Application No. 2019800347874, 6 pages.
(Continued)

*Primary Examiner* — James Sanders
(74) *Attorney, Agent, or Firm* — Scully, Scott, Murphy & Presser, P.C.

(57) ABSTRACT

A method of fabricating a casting, the method including applying a substrate to a sacrificial mold, the sacrificial mold including a shaped non-planar receiving surface to receive the substrate and provide a casting of the substrate having a shaped structure corresponding to the receiving surface; and subjecting the sacrificial mold and casting to freeze drying conditions and sublimating the sacrificial mold from the casting to form a cast article including the shaped non-planar structure.

11 Claims, 12 Drawing Sheets

(51) Int. Cl.
    *B29C 41/36*   (2006.01)
    *B29C 41/46*   (2006.01)
    *B33Y 10/00*    (2015.01)
    *B33Y 80/00*    (2015.01)
    *B29C 64/106*   (2017.01)
    *A61F 2/06*     (2013.01)
(52) U.S. Cl.
    CPC ........... *A61F 2/06* (2013.01); *A61F 2240/004* (2013.01); *B29C 64/106* (2017.08); *B33Y 10/00* (2014.12); *B33Y 80/00* (2014.12)

(56) References Cited

U.S. PATENT DOCUMENTS

| | | | |
|---|---|---|---|
| 2008/0128932 A1* | 6/2008 | Hopman | A61L 15/28 264/28 |
| 2015/0320956 A1 | 11/2015 | Dunne | |
| 2017/0343263 A1 | 11/2017 | Liao | |
| 2018/0201749 A1* | 7/2018 | Chen | C08J 9/26 |

FOREIGN PATENT DOCUMENTS

| | | |
|---|---|---|
| CN | 103861670 A | 6/2014 |
| CN | 107296983 A | 10/2017 |
| CN | 107361880 A | 11/2017 |
| CN | 107693846 A | 2/2018 |
| EP | 1341655 A2 | 9/2003 |
| JP | S62244548 A | 10/1987 |
| JP | H01-082910 A | 3/1989 |
| JP | S6482910 A | 3/1989 |
| JP | H0454042 Y | 3/1992 |
| JP | H04259509 A | 9/1992 |
| JP | 2009530042 A | 8/2009 |
| JP | 2010527646 A | 8/2010 |
| JP | 2013144403 A | 7/2013 |
| JP | 2017501810 A | 1/2017 |
| TW | I607032 B | 12/2017 |
| WO | 2015092017 A1 | 6/2015 |
| WO | 2017066727 A1 | 4/2017 |

OTHER PUBLICATIONS

Notice of Reasons for Refusal issued in Japanese Patent Application No. 2020-565294 dated Jan. 26, 2022, 5 pages.
Search Report issued in Japanese Patent Application No. 2020-565294 dated Jan. 21, 2022, 16 pages.
Supplementary European Search Report dated Feb. 3, 2022 issued in EP 19 80 7168, 4 pages.
Sooppan R. et al., "In Vivo Anastomosis and Perfusion of a Three-Dimensionally-Printed Construct Containing Microchannel Networks", Tissue Engineering: Part C 22(1):1-7 (2016).
Tamjid E. et al., "Fabrication of a Highly Ordered Hierarchically Designed Porous Nanocomposite Via Indirect 3D Printing: Mechanical Properties and In Vitro Cell Responses", Materials and Design 88:924-931 (2015).
Written Opinion of the International Searching Authority and International Search Report dated Aug. 15, 2019 received in International Application No. PCT/AU2019/050488.

* cited by examiner

METHOD OF FABRICATING A CASTING

FIELD OF THE INVENTION

The invention relates to a method of fabricating a casting using a sacrificial mold, and castings formed thereby.

BACKGROUND OF THE INVENTION

There are a large number of methods for forming castings in a wide variety of technical fields. However, depending on the methodology adopted, these methods may have a number of shortcomings including: being expensive, labour intensive, and time-consuming; being limited to a narrow range of materials; being limited to certain applications; and limitations on the material and geometric properties of the resultant casting, for example providing a casting with intricate shapes and/or fine detail.

Generally, it would be desirable to provide a relatively simple and cost effective method of forming a mold, blank, or die that could be used as a template to form a casting from a wide range of different materials in intricate shapes and with fine detail. Such a method would find use in a variety of applications and technical fields.

Notwithstanding the above, the discussion below is in respect of tissue engineering applications where tissues, such as organs, may be prepared or otherwise grown on a scaffold, which scaffolds are generally formed from a mold. The use of scaffolds and molds to form synthetic tissue provides a difficult challenge. This is because tissues themselves are a complicated combination of biological materials with sophisticated structures.

Despite enormous progress and innovation, the field has yet to meet the demand for whole tissues and organs densely populated with cells. Prevalent strategies, such as using absorbable and porous scaffolds to support and regulate cell growth and function, are constrained in size and thickness due to the diffusion limitations of oxygen, nutrients, and waste products to properly support cell viability. The body's natural pervasive vascular network addresses these limitations by providing adequate diffusion proximity for growing large tissues. However, an effective synthetic vascular system that is analogous in form and function has not yet been successfully mimicked in vitro. The natural vascular system consists of a complex network ranging from larger vessels (0.4 to 8 mm in diameter) to capillaries and micro vessels (10 to 50 μm in diameter). That the natural vascular system is hierarchical reflects the diverse functional localities along the system, which range from pressurised blood transportation, to facilitating diffusion at low flow rates. Such structures are difficult to replicate within a synthetic vascular system, such as formed using a mold or scaffold, as current materials and methodologies lack the ability to simultaneously confer mechanical strength, bioactivity, and the flexibility to be manufactured into hierarchical network structures.

Advances have been made in constructing larger vessels (larger than 6 mm diameter), primarily for transplantation and grafting purposes. Concurrently, multiple strategies have been developed to form capillaries and micro vessel networks for in vitro tissue engineering, including induced self-assembly of capillary networks and micro-patterning. However, a functional synthetic vascular system must possess both large vessels and small capillaries across a structure than ranges from linear vessels to networks and loops. This hierarchical system must demonstrate cell recruitment, oxygen and nutrient transportation, mechanical pressures and compliance, and surgical anastomosis between tissue graft and host vasculature. To date, no synthetic vascular system comprehensively satisfies these requirements.

Reference to any prior art in the specification is not an acknowledgment or suggestion that this prior art forms part of the common general knowledge in any jurisdiction or that this prior art could reasonably be expected to be understood, regarded as relevant, and/or combined with other pieces of prior art by a skilled person in the art.

SUMMARY OF THE INVENTION

In a first aspect of the invention, there is provided a method of fabricating a cast article, the method including:

applying a substrate to a sacrificial mold, the sacrificial mold including a shaped non-planar receiving surface to receive the substrate and provide a casting of the substrate having a shaped structure corresponding to the receiving surface; and subjecting the sacrificial mold and casting to freeze drying conditions and sublimating the sacrificial mold from the casting to form a cast article including the shaped non-planar structure.

The method advantageously allows a cast article to be formed in a variety of different and/or complex shapes while allowing the mold to be easily removed.

In an embodiment, sublimating the sacrificial mold to remove the sacrificial mold from the casting includes subjected the casting to a freeze-drying process.

In an embodiment, the sacrificial mold is rigid. In one form, the sacrificial mold is formed from a material that has a Young's modulus of at least 0.1 GPa. More preferably, the Young's modulus is at least 0.5 GPa. Still more preferably, the Young's modulus is at least 1 GPa. Even more preferably, the Young's modulus is at least 2 GPa. Even more preferably, the Young's modulus is at least 4 GPa. Most preferably, the Young's modulus is at least 8 GPa.

In an embodiment, the sacrificial mold is formed from a frozen material, such as ice or dry ice. In one form, the sacrificial mold includes, consists essentially of, or consists of ice. However, it will be appreciated that the sacrificial mold may include other additives, such as metal salts or dissolved organic compounds, to alter properties of the ice mold. By way of example, additives may be used to change the melting point of ice and/or to alter the affinity of the ice for the substrate that is applied to a surface thereof. In embodiments in which additives are present, it is preferred that the mold consists of ice and 0.1 wt % or less of one or more additives. More preferably, the mold consists of ice and 0.05 wt % or less of one or more additives. Most preferably, the mold consists of ice and 0.01 wt % or less of one or more additives.

The skilled addressee will appreciate that temperatures and pressures required to effect sublimation of the sacrificial mold. However, the inventors have found that a temperature in the range of from about −40° C. to −120° C. and a pressure less than about 300 μB are useful for ice. Preferably, the temperature is in the range of from about −50° C. up to about −102° C. and the pressure is less than about <250 uB pressures. The preferred temperature is −55° C. The duration of the freeze drying process varies depending on the size of the construct, but can for example be up to 16 hours.

In an embodiment, the substrate includes, consists essentially of, or consists of one or more materials selected from the group consisting of: polymers (both thermoplastic and thermosetting polymers), resins, oligomers, monomers, proteins, polypeptides, amino acids, polysaccharides, saccharides, inorganic fibres, organic fibres, plant or animal tissue, plant or animal cells, food materials, ceramic materials, composite materials including at least one of the foregoing, and mixtures thereof.

In one or more embodiments, the substrate is provided in the form of a substrate composition that includes, consists essentially of, or consists of one or more of the substrate materials listed above dispersed in a solvent. In such embodiments, it is preferred that the solvent is sublimated during the step of subjecting the sacrificial mold to freeze drying conditions.

The skilled addressee will appreciate that a wide variety of solvents may be used, and that the selection of the solvent is dependent on the material from which the substrate is formed. By way of example, a non-limiting disclosure of solvents includes: non-polar solvents such as pentane, cyclopentane, hexane, cyclohexane, benzene, toluene, 1,4-dioxane, chloroform, diethyl ether, or dichloromethane; polar aprotic solvents such as tetrahydrofuran, ethyl acetate, acetone, dimethylformamide, acetonitrile, dimethyl sulfoxide, nitromethane, or propylene carbonate; polar protic solvents such as formic acid, n-butanol, isopropyl alcohol, n-propanol, ethanol, methanol, acetic acid, or water. The preferred solvent is water as water exhibits a number of advantages over the other listed solvents. For example, water is cheap, readily available, and non-toxic. Furthermore, in preferred embodiments, where the substrate is a biological material, water is biocompatible and does not require a washing step which may be the case with other materials.

In an embodiment, wherein prior to the step of applying a substrate to the sacrificial mold, the method further includes forming the sacrificial mold by a method selected from: sculpting or machining the sacrificial mold from a solid sacrificial mold material; or casting or 3D printing a liquid mold material and solidifying the liquid mold material to form the sacrificial mold.

In an embodiment, the step of forming the sacrificial mold includes 3D printing the liquid mold material. Preferably, the step of 3D printing the liquid mold material is conducted in an environment at a temperature that is below the solidus temperature of the liquid mold material. Preferably, the temperature is at least 10° C. colder than the solidus temperature. More preferably, the temperature is at least 20° C. colder than the solidus temperature. Even more preferably, the temperature is at least 25° C. colder than the solidus temperature. Most preferably, the temperature is at least 40° C. colder than the solidus temperature. In one specific example of this embodiment where the liquid mold material is water, the step of 3D printing is carried out in a freezer set to −30° C. In another example of this embodiment where the liquid mold material is water, the step of 3D printing is carried out in a freezer set to −80° C.

In one form of the above embodiment, the liquid mold material is water. In one form, the liquid mold material includes, consists essentially of, or consists of water. In one particular form of this embodiment, the liquid mold material consists of water and 0.1 wt % or less of one or more additives. Preferably, the liquid mold material consists of water and 0.05 wt % or less of one or more additives. Most preferably, the liquid mold material consists of water and 0.01 wt % or less of one or more additives.

In forms of the above embodiment where the liquid mold material is water, suitable additives may include salts or organic compounds. The addition of salt changes the melting temperature of ice. This is useful in embodiments where the step of 3D printing the liquid mold material includes 3D printing a first mold component from a liquid mold material consisting of a liquid and one or more dissolved additives (such as at 0.1 wt % or less as described previously), and applying a second mold component to at least a portion of the first mold component, the second mold component formed from the same liquid but of different composition, such that the melting points of the first mold component and the second mold component are different. Preferably, the first mold component has a lower melting point than the second mold component. This embodiment is useful when 3D printing a first mold component of salt-water ice, before switching back to fresh-water ice for the second mold component.

In an embodiment, the receiving surface is an external receiving surface and the step of applying a substrate to the sacrificial mold includes coating at least a portion of the external receiving surface with the substrate. Preferably, the substrate is applied to the external receiving surface of the sacrificial mold by dip coating the sacrificial mold into the substrate or spray coating the substrate onto the sacrificial mold. The skilled addressee will appreciate that similar coating processes may be used.

In one embodiment, the step of applying the substrate to the sacrificial mold includes, applying a first substrate material to the receiving surface of the sacrificial mold to form a first layer of the first substrate material on the receiving layer of the sacrificial mold, and applying a second substrate material to at least a portion of the first layer to form a second layer of the second substrate material on the first layer. It will be appreciated that one or more further layers of substrate may be applied to form a multilayered substrate and/or applied to different portions of the first layer. The first substrate, the second substrate, and any further substrates may be the same or different. Where a cast article formed from a sacrificial mold has the structure of a tube or vessel, this process may enable one to vary the thickness of a wall of the tube along a length of the tube within which length the tube lumen has a more or less constant diameter. According to this embodiment, it is also possible to vary the thickness of a wall of the tube along a length of the tube within which length the tube lumen has a varying diameter.

Another option for utilising sacrificial molds for varying the wall thickness of a tube or vessel while maintaining a constant tube diameter is to utilise inner and outer sacrificial ice scaffolds. In this embodiment, inner and outer sacrificial molds are formed in an arrangement such that on application of a substrate for forming a cast article to the receiving surfaces of said molds, the inner sacrificial mold defines and forms an internal surface of a cast article and the outer sacrificial mold defines and forms an external surface of the cast article. By varying the receiving surface of the outer sacrificial mold relative to the receiving surface of the inner sacrificial mold, it becomes possible to vary the wall thickness while maintaining lumen diameter. It is also possible to provide a pattern or repeated formation on the outer wall of the cast article by forming or adapting the receiving surface of the outer sacrificial mold so as to define a pattern on an outer wall of a cast article. It is also possible to vary the thickness of a wall of the tube along a length of the tube within which length the tube lumen has a varying diameter. In one embodiment, the inner sacrificial mold may be integrally formed with the outer sacrificial mold.

Whilst there is no particular limit in respect of a wall thickness of the substrate, in an embodiment, the step of applying the substrate to the sacrificial mold to form the layer of the substrate on the surface of the sacrificial mold includes forming a layer of the substrate with a layer thickness of 10 mm or less. Preferably, the layer thickness is 7 mm or less. More preferably, the layer thickness is 5 mm or less. Even more preferably, the layer thickness is 4 mm or less. Most preferably, the layer thickness is 3 mm or less. Additionally, or alternatively, on certain forms, the wall thickness is 0.1 mm or greater.

In an embodiment, the step of applying the substrate to the sacrificial mold includes forming a tubular layer of the substrate around one or more receiving surfaces of the sacrificial mold, such as around a tubular receiving surface of the sacrificial mold.

In one embodiment, a mold comprises a shape enabling the formation of a casting or cast article from a substrate in the form of a vessel or tube when the mold is coated with the substrate. In this embodiment, the receiving surface of the mold may define a luminal surface of the vessel.

In one embodiment, a receiving surface of the mold comprises one or more grooves, slits or fissures, each groove, slit or fissure enabling the formation of a flap or membrane from a substrate on a luminal surface of a cast article or casting when the mold is coated with the substrate. Preferably the groove, slit or fissure is structured to enable the formation of a flap or membrane for controlling the velocity or direction of a fluid through a lumen of a vessel casting in which the flap or membrane is comprised. More preferably, the groove, slit or fissure is positioned on a receiving surface of a mold to form an arrangement of one or more flaps or membranes on the luminal surface of a casting that functions as a valve.

In an embodiment, prior to the step of sublimating the sacrificial mold from the substrate, the method further includes applying one or more coating layers to at least one surface of the casting, and forming a coated and/or multi-layered casting. Alternatively, or additionally, in an embodiment, after the step of sublimating the sacrificial mold from the substrate, the method further includes applying one or more coating layers to at least a portion of the surface of the cast article, and forming a coated and/or multilayered cast article. It will be appreciated that one or more coating layers may be applied to form a multilayered coating and/or applied to coat different portions of the surface of the casting and/or cast article. The one or more coating layers may be formed from the same material as the substrate or a different material.

In an embodiment, the casting and/or cast article includes at least one portion exhibiting a tube-like shape.

In a second aspect of the invention, there is provided a method of fabricating a cast biomaterial with internal hierarchical structure, the method including:

coating a biomaterial composition onto at least a portion of an external receiving surface of a sacrificial ice mold having a hierarchical structure and forming a casting of the biomaterial composition on the external surface of the ice mold, the casting having an internal hierarchical structure corresponding to the external receiving surface of the sacrificial ice mold; and subjecting the casting to a temperature and pressure to lyophilise the sacrificial ice mold from the casting to form a cast biomaterial with internal hierarchical structure.

In a third aspect of the invention there is provided a method of fabricating a casting or cast article having a hierarchical structure, the method including:

coating at least a portion of a hierarchical structure of an external surface of a sacrificial mold with a substrate in conditions for forming a casting having a hierarchical structure defined by the external surface of the mold from the coating; and subjecting the casting and/or mold to conditions for disintegrating the mold enabling release of the casting from the mold;

thereby fabricating a casting having a hierarchical structure.

In one embodiment of the third aspect there is included the step of cross linking or curing the substrate that has been applied onto the at least a portion of an external receiving surface of the mold, said cross linking or curing of the substrate thereby forming on the mold a casting having a hierarchical structure defined by the external surface of the mold.

In one embodiment the casting and or mold is subject to conditions for sublimating or lyophilising the mold, thereby disintegrating the mold to release the casting from the mold.

In an embodiment, the step of subjecting the casting to a temperature and pressure to lyophilise the sacrificial ice mold from the casting includes subjecting the casting to a freeze-drying process.

Whilst there is no particular limit in respect of a wall thickness of the casting and/or cast biomaterial, in an embodiment, the casting and/or cast biomaterial has a wall thickness of 10 mm or less. Preferably, the wall thickness is 7 mm or less. More preferably, the wall thickness is 5 mm or less. Even more preferably, the wall thickness is 4 mm or less. Most preferably, the wall thickness is 3 mm or less. Additionally or alternatively, on certain forms, the wall thickness is 0.1 mm or greater or from 0.1 to 1.0 mm, or 0.3, or 0.6 or 0.9 mm.

In an embodiment, the casting or cast biomaterial is a free standing hierarchical vascular structure.

In an embodiment, the hierarchical structure of the casting includes at least a parent vessel, a plurality of daughter vessels extending from a terminal end of the parent vessel, and in certain forms, a plurality of granddaughter vessels extending from a terminal end of one or more or each of the daughter vessels. It will be appreciated that further branching is possible, such as to provide granddaughter and great granddaughter vessels (and so on). It is preferred that the hierarchical structure (if present) obeys Murray's law. That is, when a parent blood vessel branches into daughter vessels, the cube of the radius of the parent vessel is equal to the sum of the cubes of the radii of daughter blood vessels.

The daughter, granddaughter, and great granddaughter vessels may be in the form of vascular structures including loops, bifurcations, multifurcation, and/or combinations thereof. For the purpose of clarity, the term hierarchical structure includes a structure having both diverging and converging daughter, granddaughter, and great granddaughter vessels, e.g. two or more smaller diameter vessels converging together to form one larger diameter vessel.

In one embodiment a vessel may have a closed end.

An advantage of the present method is that it allows the formation of narrow vessels. In a preferred form, the hierarchical structure includes at least one vessel having a cross-sectional area corresponding to a diameter of 2 mm or less. Preferably, the cross-sectional area corresponds to a diameter of 1.5 mm or less. More preferably, the cross-sectional area corresponds to a diameter of less than 1 mm or less. Most preferably, the cross-sectional area corresponds to a diameter of 0.5 mm or less. There is no particular upper size limit to the diameter of any particular vessel in the hierarchical structure formed using this method. The largest vessel of the vascular system in the human body is the aorta which has a diameter of around 20 mm. It will be appreciated that other animals possess larger diameter vessels and the method can be used to form these larger vessels. In other embodiments, the diameter may be larger than 20 mm, for example from 25 to 50 mm, particularly where a vessel structure for other than the vascular system is required.

In an embodiment, the substrate is applied to the external receiving surface of the sacrificial mold by dip coating the external receiving surface of the sacrificial mold into the substrate or spray coating the substrate onto the external receiving surface of the sacrificial mold. The skilled addressee will appreciate that similar coating processes may be used.

In an embodiment, wherein prior to the step of coating a substrate or biomaterial onto at least a portion of the external receiving surface of the sacrificial ice mold, the method further includes forming the sacrificial ice mold by 3D printing water to form the sacrificial ice mold.

In one form of the above embodiment, the step of 3D printing the liquid mold material is conducted in an environment at a temperature that is at least 5° C. colder than the solidus temperature of the liquid mold material. Preferably, the temperature is at least 10° C. colder than the solidus temperature. More preferably, the temperature is at least 20° C. colder than the solidus temperature. Even more preferably, the temperature is at least 25° C. colder than the solidus temperature. Most preferably, the temperature is at least 40° C. colder than the solidus temperature. In one specific example of this embodiment where the liquid mold material is water, the step of 3D printing is carried out in a freezer set to −30° C. In another example of this embodiment where the liquid mold material is water, the step of 3D printing is carried out in a freezer set to −80° C.

In another form of the above embodiment, the step of 3D printing the liquid mold material includes depositing the liquid mold material and spraying the liquid mold material with liquid nitrogen to freeze the liquid mold material.

In an embodiment, the step of applying the substrate or biomaterial composition to the sacrificial mold includes, after applying the substrate or biomaterial composition, applying a further material to at least a portion of the cast or biomaterial cast layer to form a layer of the further material on a surface of the cast or biomaterial cast layer. It will be appreciated that further layers of further material may be applied to form a multilayered substrate on the surface of the biomaterial composition and/or applied to different portions of the first layer. The biomaterial, the substrate, and any further substrates may be the same or different.

In an embodiment, after the step of lyophilising the sacrificial ice mold, the method further includes applying one or more coating layers to a surface of the cast biomaterial, and forming a coated and/or multilayered cast biomaterial. It will be appreciated that one or more coating layers may be applied to form a multilayered coating and/or applied to coat different portions of the surface of the cast biomaterial. The one or more coating layers may be formed from the same material as the cast biomaterial or a different material.

In an embodiment, the method initially includes obtaining an image of a vascular structure, and 3D printing a negative ice mold of that vascular structure. The image may be obtained, for example, from a CT/MRI scan of a patient's vascular structure, or from a database of vascular structures. In this way, the method of the invention provides a bespoke process for preparing a vascular (or other) structure.

In an embodiment of the second or third aspects of the invention, where the casting or cast article includes a vessel or tube conformation, the wall thickness may vary across a region of fixed luminal diameter as described in relation to the first aspect of the invention, or the wall thickness may vary across a region of varying luminal diameter.

In an embodiment of the second or third aspects of the invention, where the casting or cast article includes a vessel or tube conformation, the luminal surface may be provided with one or more flaps or membranes for controlling fluid velocity or direction, as described in relation to the first aspect of the invention.

In a fourth aspect of the invention, there is provided a cast article, such as a cast biomaterial, fabricated according to the method of the first, second or third aspects of the invention, and embodiments thereof.

In a fifth aspect of the invention, there is provided a hierarchical vascular structure formed according to the method of the first, second or third aspects of the invention, and embodiments thereof.

In a sixth aspect of the invention there is provided a cast article suitable for use in a vascular system, the cast article being formed according to the method of the first, second or third aspects of the invention and including:
  a first layer having an inner surface defining a vessel lumen, said first layer being composed of a porous polymer enabling diffusion of nutrients and/or gas to and from the vessel lumen;
  a second layer formed on an outer surface of the first layer, said second layer enabling vascular cell infiltration and/or attachment;
  and optionally:
  a third layer formed on an outer surface of the second layer, said third layer for providing mechanical strength to the cast article and enabling strength for suturing and suture retention.

In one embodiment, the first layer may include agarose, the second layer may include an extracellular protein such as an elastin or a collagen and/or one or more cells such as a fibroblast or endothelial cell, and the third layer may include a synthetic polymer such as polycaprolactone.

Preferably the cast article is suitable for use in an arterial or venous system. The article may be suitable for use in a lymphatic system. Further aspects of the present invention and further embodiments of the aspects described in the preceding paragraphs will become apparent from the following description, given by way of example and with reference to the accompanying drawings.

Finally, heat stabilisation of the tropoelastin substrate coating resulted in a tropoelastin vascular structure.

Figures 1A, 1B, 1C, 1D, 1E:
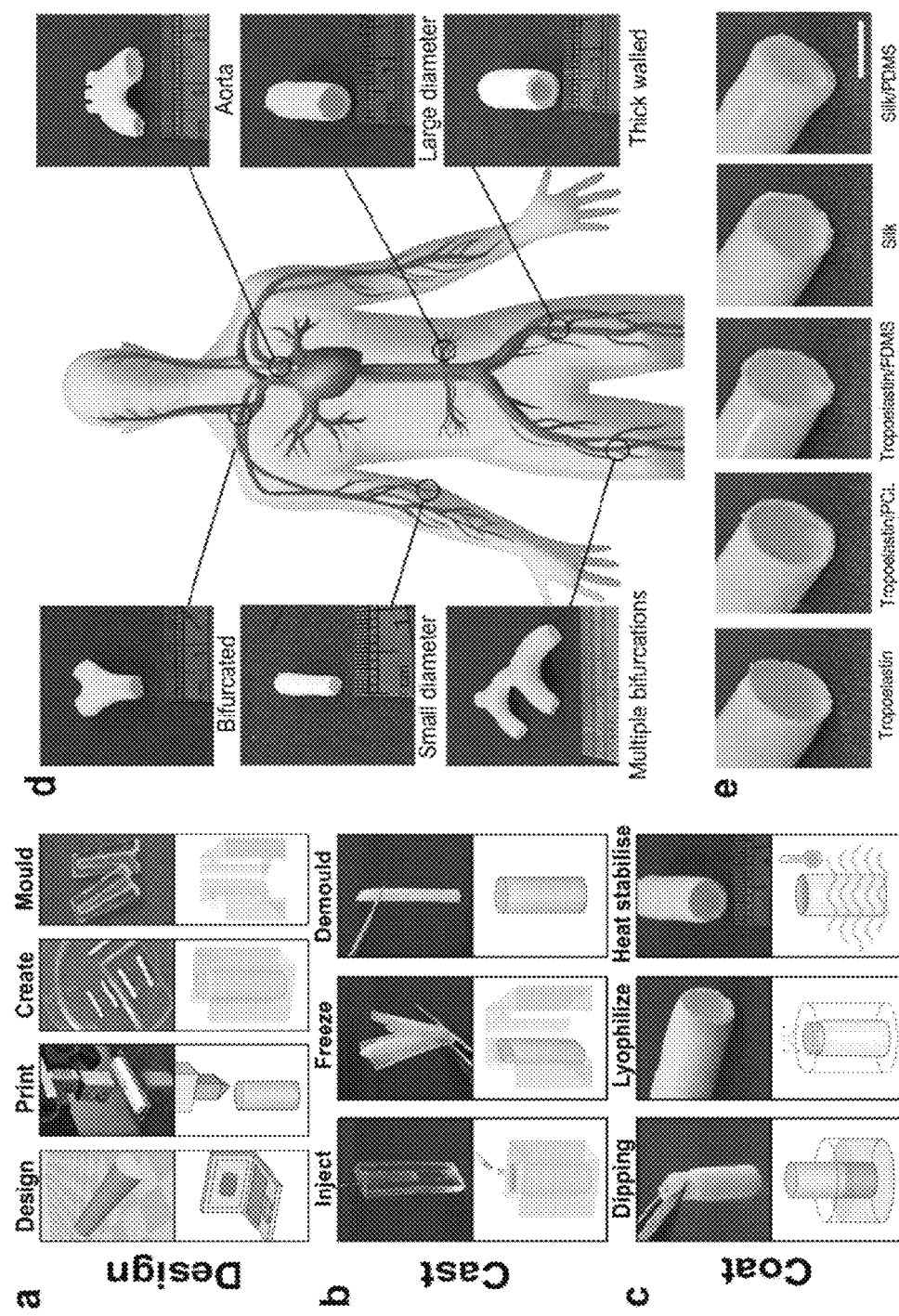
FIG. 1a illustrates a design stage in which a positive mold was first digitally designed and 3D printed before being immersed in polydimethylsiloxane (PDMS) to create the negative mold.
FIG. 1b illustrates the casting stage in which water was injected into the PDMS mold before being snap frozen, forming a sacrificial mold made of ice.
FIG. 1c illustrates that coating stage in which the sacrificial ice mold was dip coated with a substrate, in this case dissolved tropoelastin. The substrate-coated sacrificial mold was snap frozen to solidify this substrate coating. Subsequent lyophilisation removed the sacrificial ice mold without affecting the substrate coating.

FIG. 1d illustrates that a broad range of vascular structures can be made using this method including bifurcating vessels, small diameter linear vessels, multiple bifurcating vessels, aortic arch, larger diameter linear vessels, and thick-walled vessels.

FIG. 1e illustrates a range of substrate materials that can be coated onto the sacrificial ice molds, including, but not limited to, tropoelastin, tropoelastin combined with polycaprolactone (PCL), tropoelastin combined with PDMS, silk, and silk combined with PDMS.

Figures 2A, 2B, 2C, 2D, 2E, 2F, 2G, 2H, 2I:
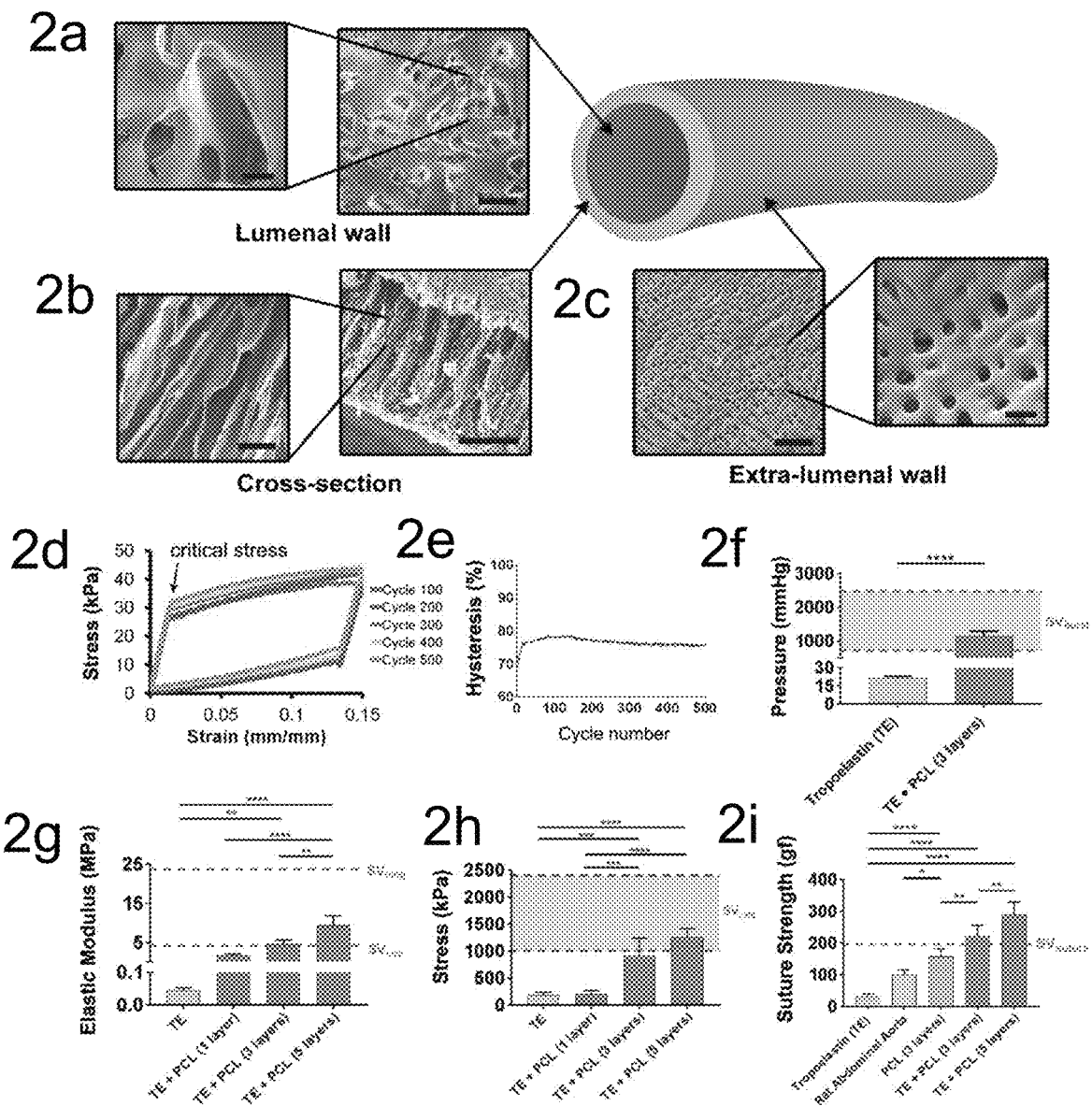

FIG. 2a is an SEM image of the luminal surface of tropoelastin vessels having pores less than 10 µm in diameter (Scale bar, 10 µm). The zoomed image reveals that that these pores were connected to the substructure within the vessel walls (Scale bar, 2 µm).

FIG. 2b is an SEM image of the cross-section of tropoelastin vessels exhibiting channels that were radially connected between the luminal and extra-luminal walls (Scale bar, 100 µm). The zoomed image shows the radially aligned channels were approximately 2 µm in width (Scale bar, 2 µm).

FIG. 2c is an SEM image showing the extra-luminal surface of tropoelastin vessels had pores that were smaller than the pores on the luminal surface (Scale bar, 10 µm). The zoomed image shows that pores on the extra-luminal surface were typically less than 2 µm in diameter and also connected to the substructure within the vessel walls (Scale bar, 2 µm).

FIG. 2d are representative stress-strain curves of cyclic testing of tropoelastin vessels. The superimposed curves across 500 cycles indicated there was no sign of mechanical degradation and that elasticity was preserved. The material exhibited a bi-phasic loading phase with initially high stiffness that subsequently decreased, and initially low compliance that subsequently increased. The point at which stiffness and compliance changed was termed the critical stress.

FIG. 2e is a graph exhibiting hysteresis was evident, and was also consistent throughout cyclic testing, attesting to preservation of mechanical properties over the duration of the test.

FIG. 2f is a graph showing the burst pressure of tropoelastin vessels was significantly improved through the addition of PCL as a secondary substrate. This was comparable to the burst pressure of human saphenous veins (grey zone).

FIG. 2g is a graph showing the elastic modulus of tropoelastin vessels was significantly improved through the addition of PCL. 3 layers of PCL was required to provide an elastic modulus comparable to that of the human saphenous vein. Error bars represent standard deviation, p-values: * <0.05,  <0.01, * <0.001, **** <0.0001.

FIG. 2h is a graph showing the ultimate tensile strength (UTS) of tropoelastin vessels was significantly improved through the addition of PCL. 5 layers of PCL resulted in UTS comparable to that of the human saphenous vein. Error bars represent standard deviation, p-values: * <0.05,  <0.01, * <0.001, **** <0.0001.

FIG. 2i is a graph showing suture retention strength improved through the addition of PCL, which was stronger compared to rat abdominal aorta and the human saphenous vein. Error bars represent standard deviation, p-values: * <0.05,  <0.01, * <0.001, **** <0.0001.

Figures 3A, 3B, 3C, 3D, 3E, 3F, 3G:
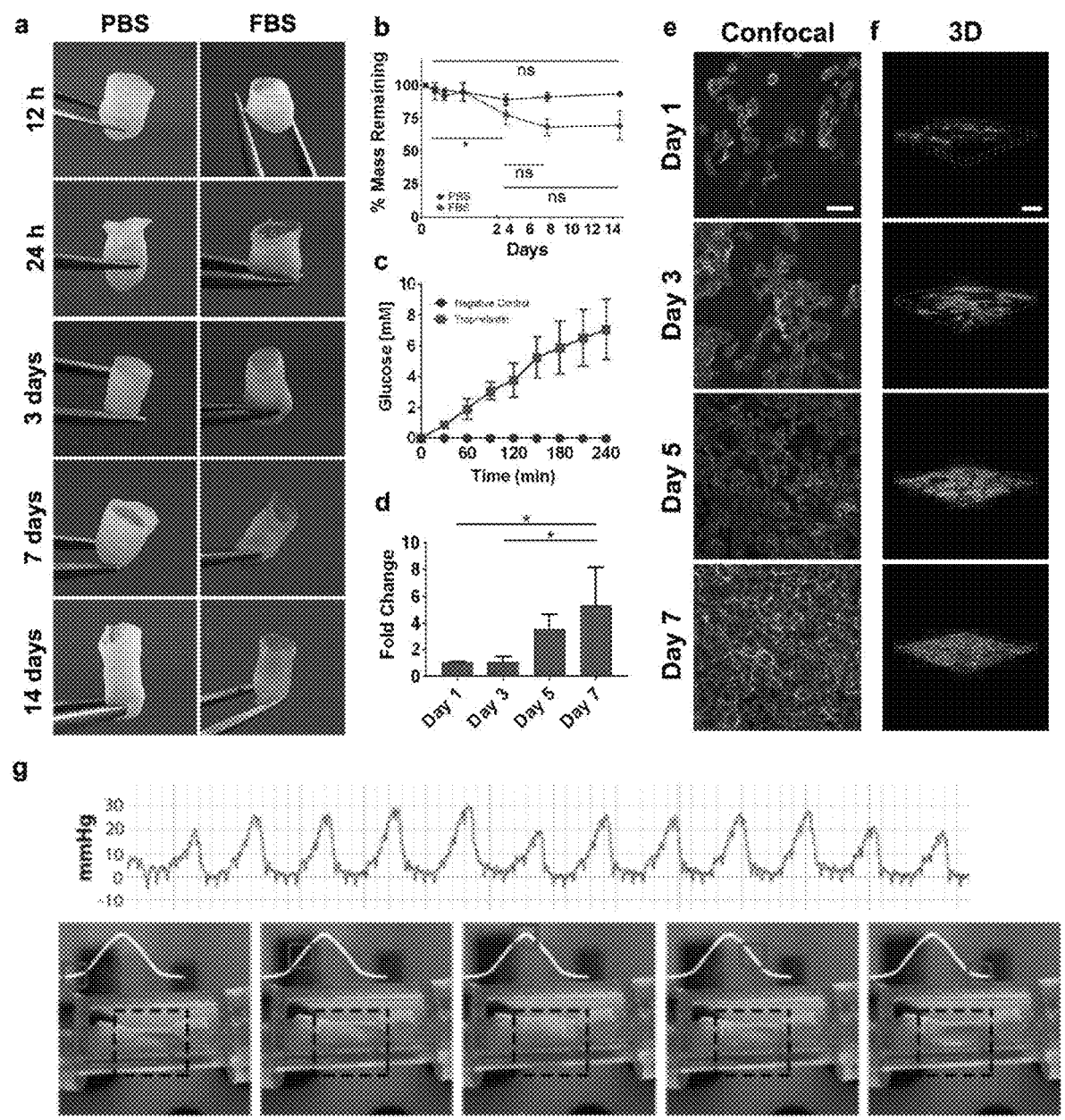

FIG. 3a illustrates a 2-week degradation assay of vessels incubated in either 100% foetal bovine serum (FBS) or phosphate buffer solution (PBS) demonstrated preservation of structural integrity.

FIG. 3b is a graph showing as retention analysis of tropoelastin vessels during the 2-week degradation being incubated in FBS or PBS. This mass loss stabilised after 3 days, with no significant mass loss observed between day 3 and day 14 in vessels incubated in FBS. Error bars represent standard deviation, p-values: * <0.05,  <0.01, * <0.001, **** <0.0001.

FIG. 3c is a graph showing that over the course of 4 h, as glucose-infused PBS was pumped through the tropoelastin vessel, glucose concentrations measured in the extra luminal space increased. Error bars represent standard deviation, p-values: * <0.05,  <0.01, * <0.001, **** <0.0001.

FIG. 3d is a graph showing DNA quantification of human umbilical vein endothelial cells (HUVECs) proliferating on the luminal surface of tropoelastin vessels indicated a significant increase in cell population between day 1 and day 7. Error bars represent standard deviation, p-values: * <0.05,  <0.01, * <0.001, **** <0.0001.

FIG. 3e is a series of confocal microscopy images of HUVEC proliferation on the luminal surface of tropoelastin vessels. The HUVEC population grew to confluence over the 7-day proliferation duration (Scale bar, 100 µm).

FIG. 3f is a series of 3D z-stack views demonstrated the HUVECs forming a characteristic monolayer (Scale bar, 100 µm).

FIG. 3g is a graph showing that the pulsatile pressure wave caused the tropoelastin vessel to expand and dilate. Sequential photos taken during one pressure wave showed the tropoelastin vessel demonstrating total elastic recoil and no observation of physical deformation.

Figures 4A, 4B, 4C, 4D:
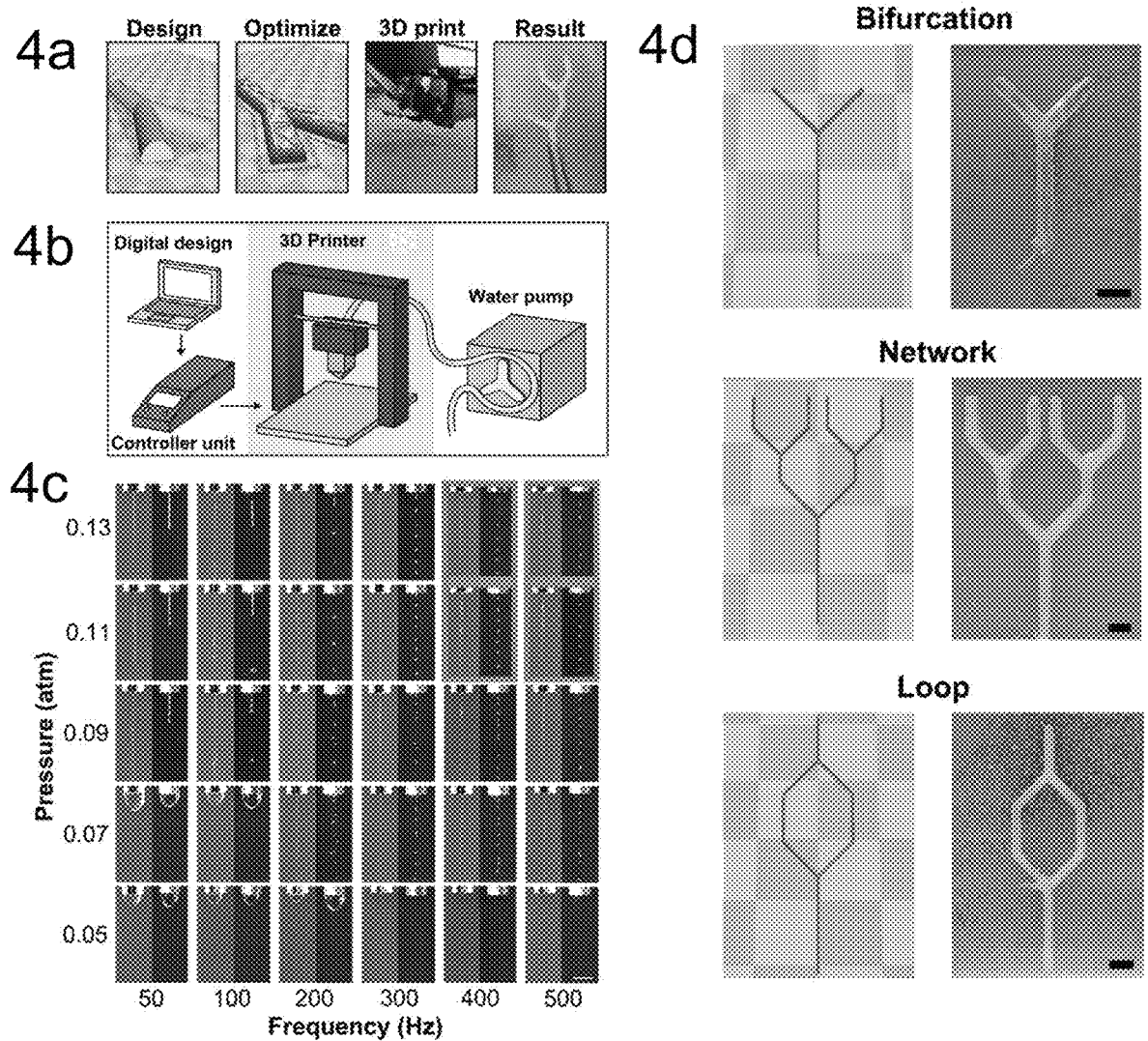

FIG. 4a illustrates a digital design of a vascular structure that was digitally designed and optimized for ice printing before the printing instructions were sent to the 3D printer to accurately print the sacrificial ice mold.

FIG. 4b is a schematic showing the 3D printer assembly. The 3D printer was housed within a subzero environment to facilitate printing ice. The 3D printer controller and water delivery pump were positioned outside of the subzero ambient environment to prevent damage and freezing of the water in the delivery line.

FIG. 4c shows the optimisation of the 3D printing conditions. Consistent droplet generation is required for high fidelity printing, and was achievable with certain combinations of pressure and actuation frequency (highlighted) (Scale bar, 5 mm).

FIG. 4d illustrates that the fidelity of the 3D printer was sufficient to fabricate ice sacrificial molds of basic vascular system shapes including bifurcations, networks, and loops (all scale bars, 2 mm).

Figures 5A, 5B, 5C, 5D, 5E, 5F, 5G, 5H, 5I:
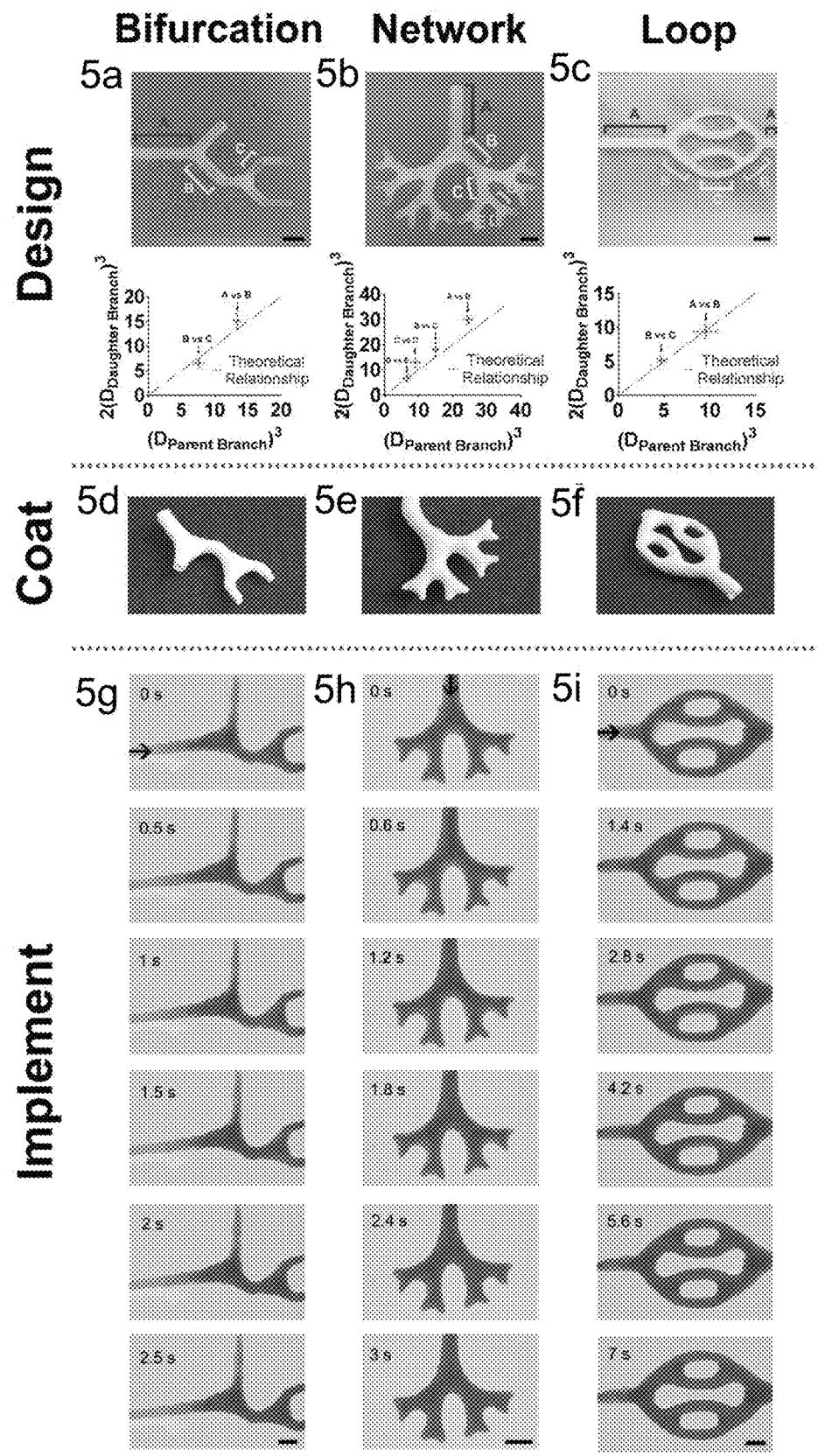

FIG. 5a illustrates bifurcating vascular designs (Scale bar, 4 mm).

FIG. 5b illustrates vascular network designs (Scale bar, 4 mm).

FIG. 5c illustrates vascular loop designs (Scale bar, 4 mm).

FIGS. 5d-f show images of silk coated castings of ice molds of the vascular structures of FIGS. 5a-c, respectively.

FIGS. 5g-i show images of liquid flow through the vascular structures shown in FIGS. 5d-f, respectively.

Figure 6:
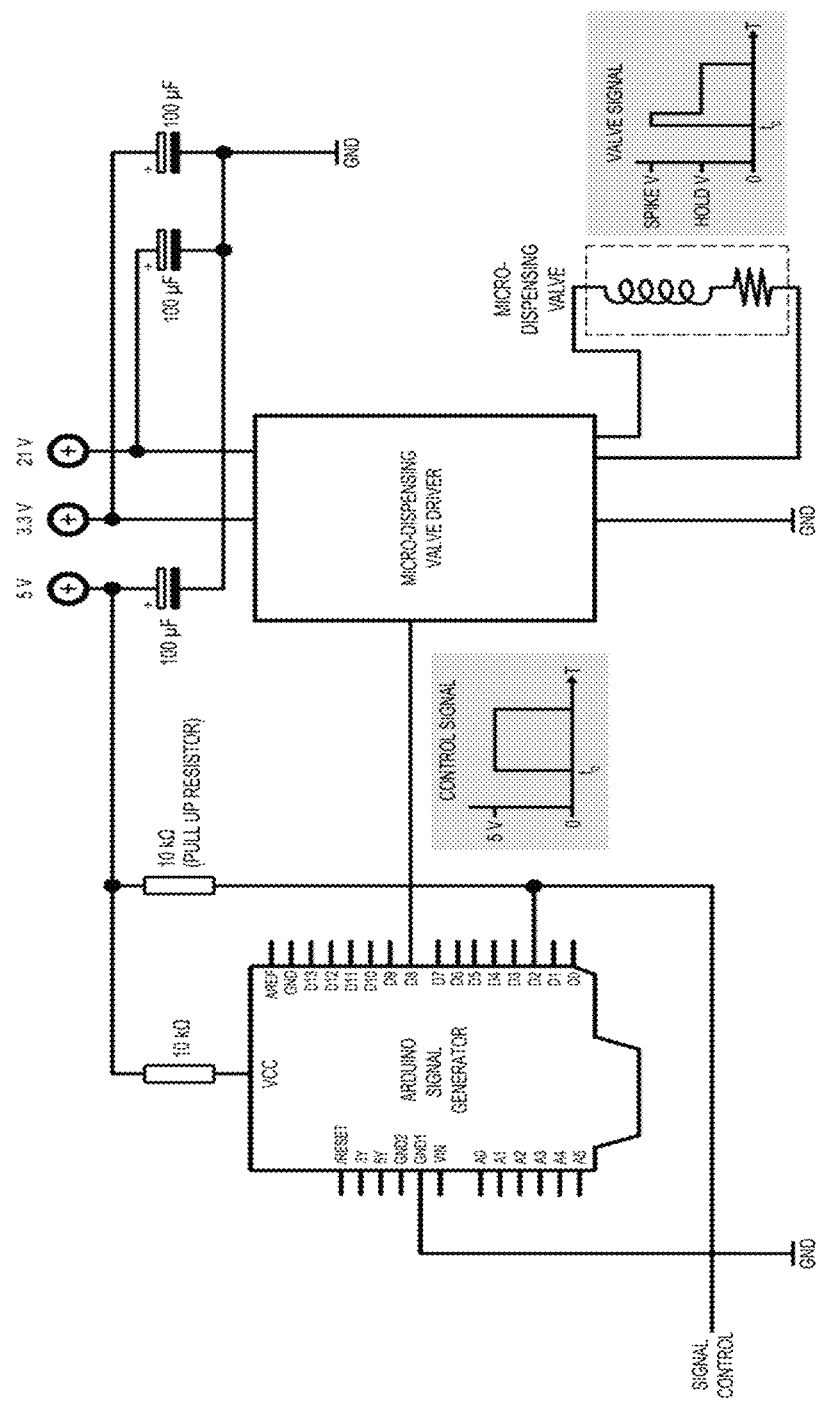

FIG. 6 is a schematic of the driving electronics for a micro-dispensing valve.

Figure 7:
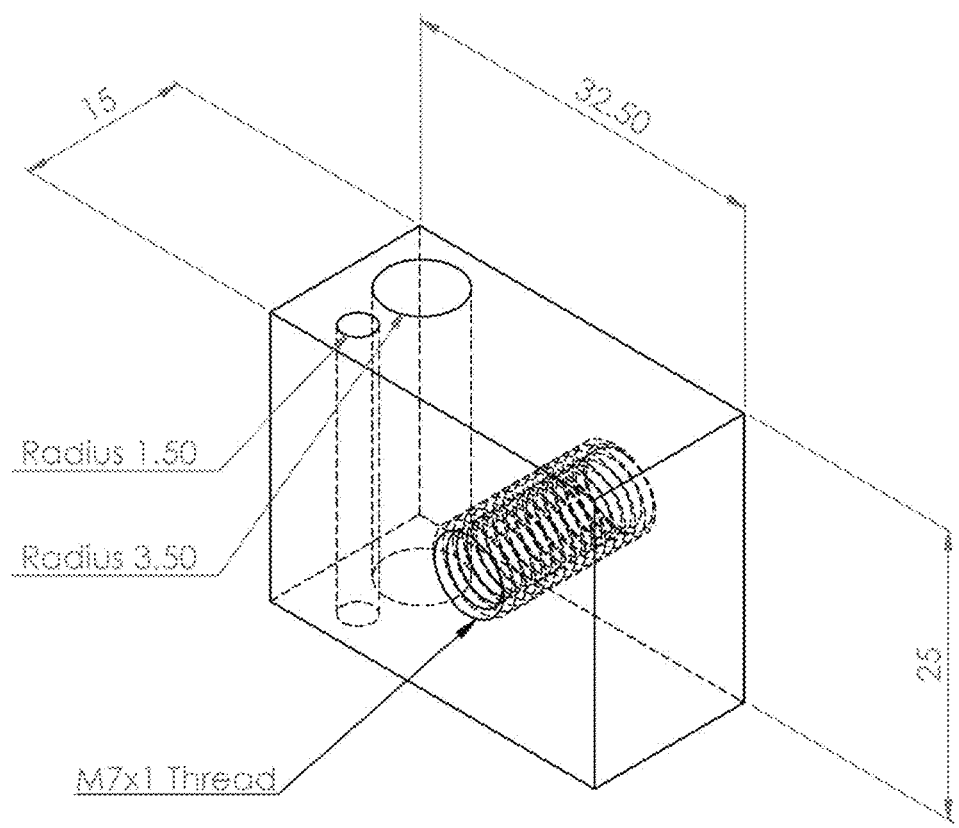

FIG. 7 is a schematic of a print-head block (all dimensions in millimetres).

Figure 8:
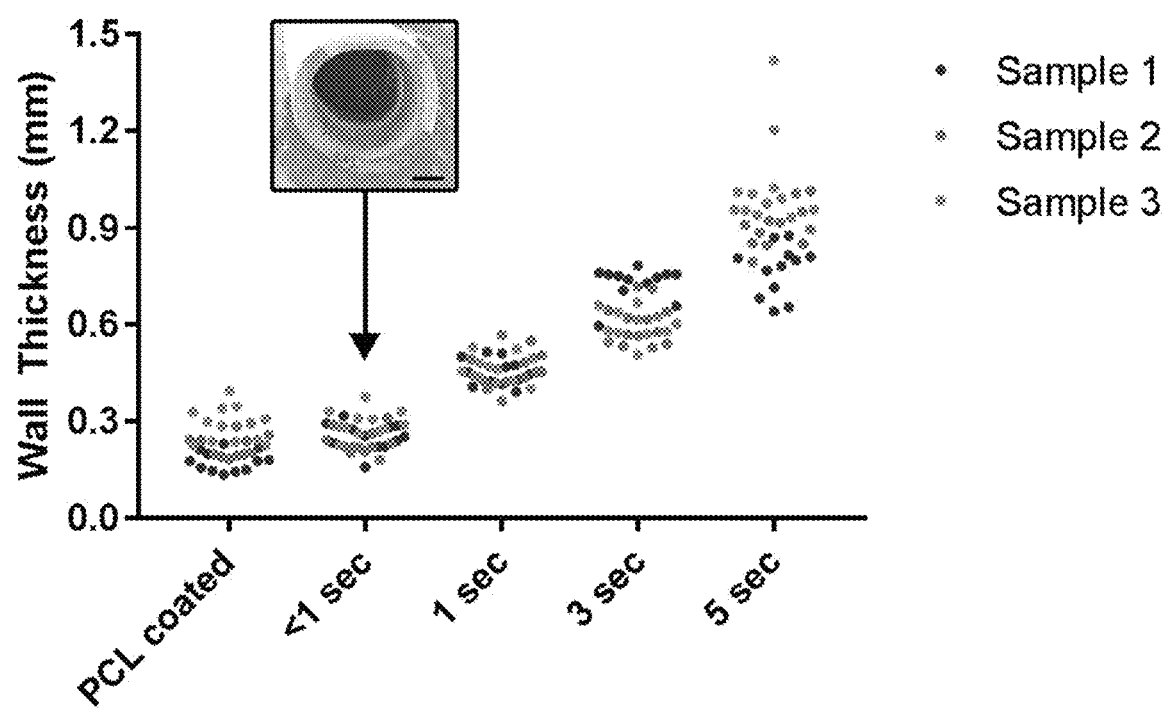

FIG. 8 is a scatter plot of wall thickness measurements of a casting. (The scale bar, 500 µm).

Figure 9:
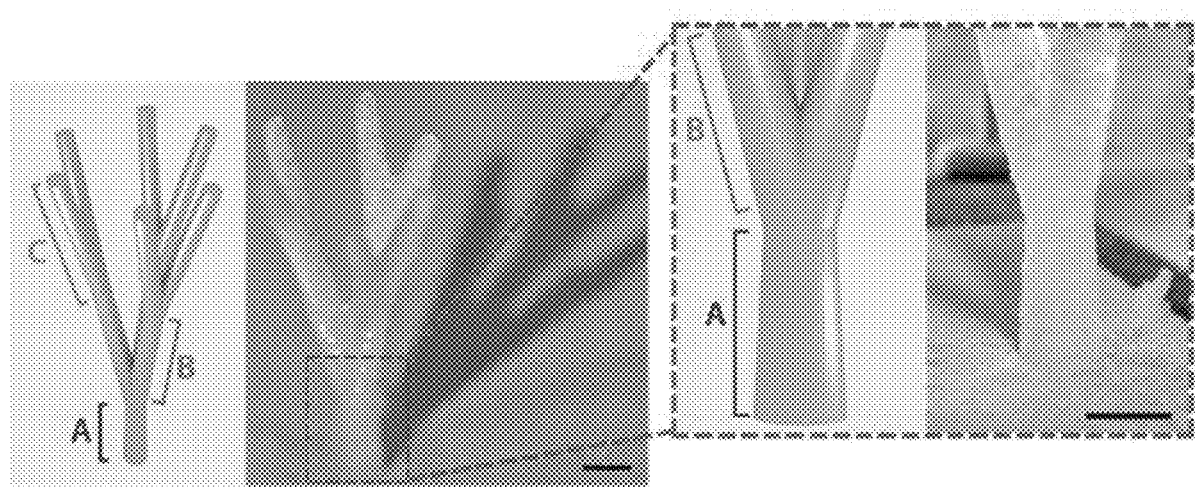

FIG. 9 is an image of a 3 dimensional mold formation. (Scale bar, 4 mm).

Figure 10:
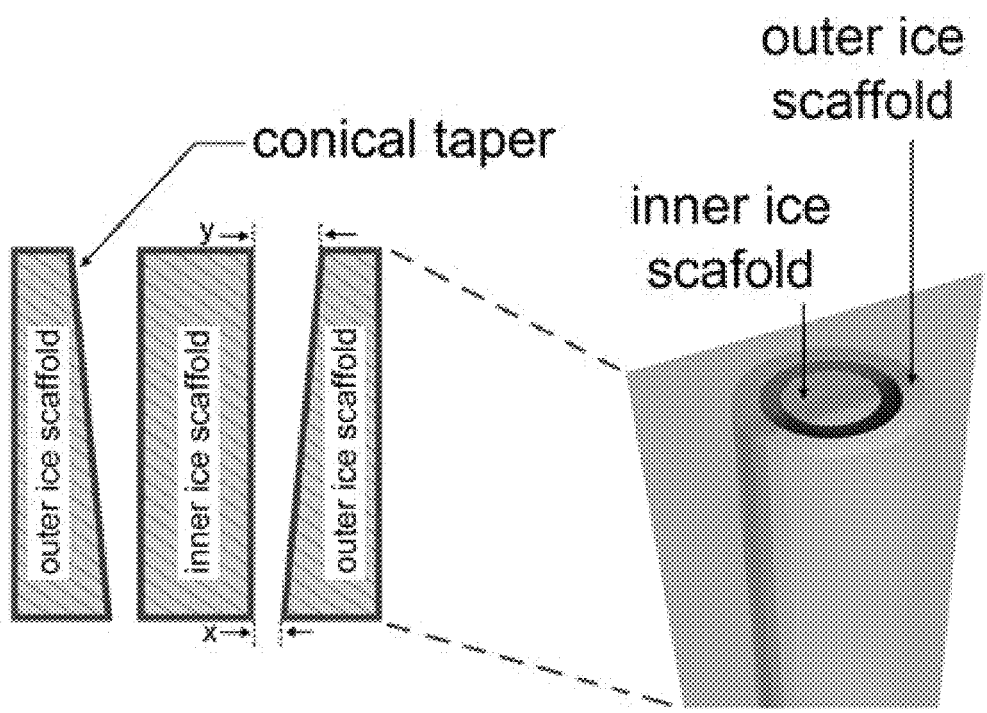

FIG. 10 is an image describing inner and outer ice scaffolds for forming casting having differential wall thickness.

Figure 11:
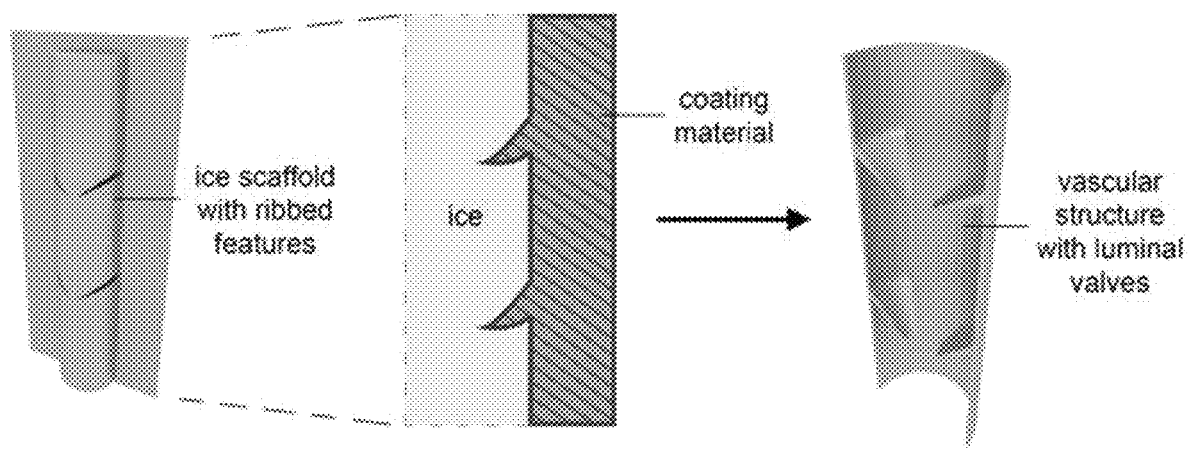

FIG. 11 is an image showing an ice scaffold having one or more grooves for formation of a casting containing internal valve structures.

Figure 12:
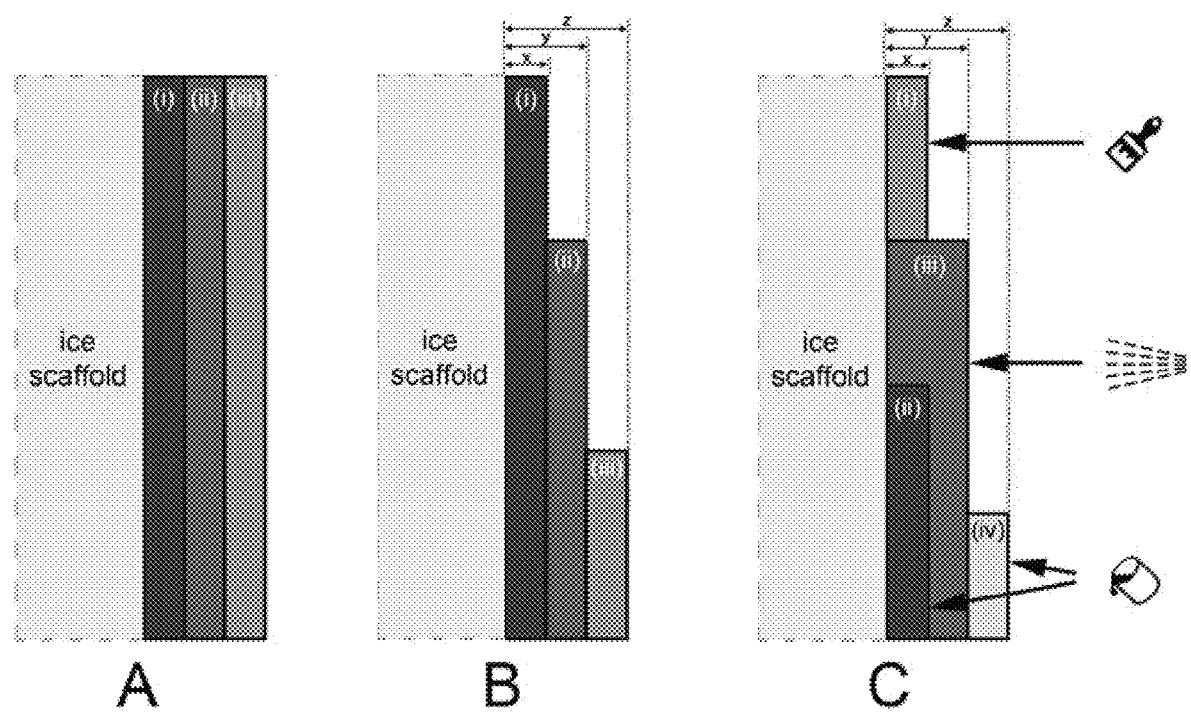

FIG. 12 is a schematic showing selective coating of ice scaffolds.

DETAILED DESCRIPTION OF THE EMBODIMENTS

The invention relates to a method for forming a cast article that broadly includes applying a substrate to a receiving surface of a sacrificial mold to form a casting of the substrate on the sacrificial mold; and sublimating the sacrificial mold to remove the sacrificial mold from the casting and form a cast article.

This method may be applied to form castings from a wide range of materials. However, in preferred forms of the invention, the sacrificial mold is formed from ice. Given this, the method finds particular use with substrates that can be applied at a temperature sufficient to minimise melting the ice mold, such as at a temperature of 10° C. or less. Preferably, the substrate is applied at a temperature of 4° C. or less.

The substrate is generally applied to the sacrificial mold in the form of a liquid. The substrate may itself be a liquid (for example, one which solidifies on contact with the sacrificial mold or solidifies/gels at higher temperatures), or dissolved within a liquid solvent. Alternatively, the substrate may be provided in the form of a powder, such as by powder coating the sacrificial mold. Suitable substrates include polymers (both thermoplastic and thermosetting polymers), resins, oligomers, monomers, proteins, polypeptides, amino acids, polysaccharides, saccharides, inorganic fibres, organic fibres, plant or animal tissue, plant or animal cells, food materials, ceramic materials, composite materials including at least one of the foregoing, and mixtures thereof.

After the substrate has been applied to the sacrificial mold to form a substrate coated sacrificial mold (such as by dip coating or spray coating or other similar process), the substrate may be subjected to further treatment processes, for example the substrate may be subjected to surface treatment processes and/or coated with additional layers. By way of example, the substrate may be subjected to a curing reaction or a cross-linking reaction. The skilled addressee will appreciate that the curing or cross-linking reaction may for example involve exposing the substrate to one or more further reactants, UV light, or other stimulus.

Subsequently, the substrate coated sacrificial mold is exposed to temperature and pressure conditions to cause the sacrificial mold to sublimate from the substrate and form the casting. Again, in a preferred form of the invention the sacrificial mold is formed from ice. The triple point of water is at 273.16 K and a partial vapour pressure of 611.657 pascals. Thus, sublimation from ice to water vapour is at an appropriate temperature and pressure below these values. Conveniently, this step of sublimating or lyophilising the ice may be carried out in a freeze-dryer. The skilled person will appreciate that the sacrificial mold may be made from other materials that sublimate at a useful temperature and pressure range.

The sacrificial mold may be prepared by casting or 3D printing. That is, in one or more forms, a liquid mold material may be cast or printed and solidified to form the sacrificial mold. Notwithstanding this, the inventors have found that the use of 3D printing can provide a sacrificial mold with fine and detailed features. Such a sacrificial mold is particularly useful in a biological setting, such as in the preparation of a mold for producing vascular tissue.

The invention will be described and exemplified below in relation to the preferred embodiment of a method for forming a fabricating a casting of a biomaterial with an internal hierarchical structure. The method broadly includes the steps of coating a biomaterial onto at least a portion of an external surface of a sacrificial ice mold having a hierarchical structure and forming a casting of the biomaterial on the ice mold, the casting having an internal hierarchical structure corresponding to the external surface of the sacrificial ice mold; and subjecting the casting to a temperature and pressure to lyophilise the sacrificial ice mold from the casting. The skilled addressee will appreciate that while the method is illustrative of particular embodiments, the invention is not intended to be limited by such materials, application, and methodology.

EXAMPLES

The concepts and methods described herein are particularly useful for engineering entire hierarchical vascular systems. In such embodiments, the use of ice to fabricate sacrificial molds, onto which biological and synthetic materials may be coated to form a vascular structure, is particularly relevant. By using ice, the method is simple, cost-effective, and adaptable to other coating materials. Moreover, ice does not leave behind toxic residues, resulting in a completely clean and biocompatible manufacturing process. These advantageous properties simplify the fabrication process, streamline regulatory approval, and encourage upscale manufacturing in the future.

Compared to other softer polymers that have been previously used for sacrificial molds, ice also possesses the required structural rigidity for creating well-defined shapes and dimensions with high fidelity. Using these properties, the inventors developed the technology to cast and 3D print ice molds that can be made with fine details, higher resolution, and complexity. Using these techniques, the creativity and scope of designs of functional vascular structures that can be fabricated is extended. Along with the ability to fabricate complex vascular shapes, in these specific examples, there is also the requirement to ensure proper conditions for dynamic blood flow.

Method of Cast Ice Molds for Fabrication of Vasculature

Present herein is the use of cast ice molds for fabricating blood vessels. Ice is completely biocompatible, easily removed through lyophilisation, free from toxic compounds or residues, and possesses the structural rigidity to allow complex and freestanding vascular architectures to be engineered with high fidelity. This is advantageous over traditional approaches of hydrogel or bioink based sacrificial molds, which have difficulty in creating freestanding vascular designs and require multiple washing steps to remove residue that may be toxic to cells. Moreover, the accessibility to water as a fabrication material is not cost or quantity prohibitive, presenting unique opportunities for efficient commercial upscaling.

Ice is a versatile material from which to form the sacrificial mold as ice (or water as the case may be) may be cast and 3D printed to form the sacrificial ice molds, depending on the requirements of resolution and complexity of different vascular designs. These sacrificial molds can additionally be coated with a variety of different materials with which to form the synthetic vessel wall.

To demonstrate the versatility of this method, the inventors investigated key questions that validated the functionality of blood vessels fabricated in this manner. Specifically, the inventors show that: (a) this method has the flexibility to create vascular structures in a range of sizes and shapes with varying degrees of complexity; (b) this method is compatible with using a variety of materials to form the vascular wall; (c) the blood vessels are engineered with high precision and can be designed to facilitate non-turbulent bifurcating fluid flow; (d) the fabricated vascular flow systems can be tuned to sustain pressurised blood flow, surgical handling for anastomoses, and viable glucose nutrient delivery; and (e) the use of tropoelastin provides a biocompatible vascular wall that supported human umbilical vein endothelial cell proliferation. Collectively, the reported experimental and theoretical findings demonstrate a new platform fabrication system for the design and engineering of hierarchical vascular structures to support not only complex engineered tissues but also patient-customised vascular grafts, for example from a CT/MRI scan of a patient's vessels to drive the 3D printing replication.

While a large range of materials may be used as the substrate, this example primarily focusses on the use of tropoelastin as the main material to coat the ice molds and to build the vascular wall of engineered blood vessels. Tropoelastin is the building block of elastin, the most prevalent and durable component in the mammalian vascular extracellular matrix. Towards the demanding goal of bio fabricating artificial blood vessels, tropoelastin is a highly attractive material candidate as it: (i) has the versatility to be both enzymatically and non-enzymatically cross-linked into a myriad of elastin-based materials, (ii) possesses the correct biological signalling for a vascular role by promoting endothelialisation through recruiting human coronary artery and microvascular endothelial cells, (iii) prevents intimal hyperplasia and restenosis, (iv) promotes angiogenesis, and (v) and can be stored dry for long term shelf life, with subsequent conversion to its natural elastic state on hydration.

In the present example, the process of casting ice molds can be broken down into three main stages of designing, casting, and coating. During the designing stage (FIG. 1a), custom positive molds were digitally designed and 3D printed. This gives the flexibility for a range of vascular structures to be designed. The 3D printed positive mold was then immersed in polydimethylsiloxane (PDMS) to produce an inert and reusable negative mold. During the casting stage (FIG. 1b), water was injected into the negative mold and snap frozen to form ice in the shape of the original digital design. The use of snap freezing is optional. However, snap freezing speeds up the process considerably compared with leaving the water-filled PDMS mold in a freezer.

The ice could then be demolded from the PDMS to be used as a sacrificial mold. However, the act of demolding increases in difficulty for very thin ice molds due to the brittleness of the ice. As such, this casting method is best suited for larger diameter vascular designs. Once the sacrificial ice scaffold has been either removed from the PDMS mold or from the print-bed if it was 3D printed, it is optionally subjected to a further snap freezing process, such as in liquid nitrogen. This helps to ensure that the ice mold is fully frozen prior to the coating process.

In the final stage of coating (FIG. 1c), the ice mold was dip coated with dissolved tropoelastin to form the wall of a vascular structure. The substrate-coated ice mold was snap frozen again to solidify the material coating. The coating process can be conducted at normal ambient temperatures and conditions. In this example, the dissolved substrate itself is at a temperature of <10° C. This is so that, once the substrate is in contact with the ice, the temperature difference minimises the melting of the ice.

A process for assessing the wall thickness of tropoelastin-based castings is now described. Briefly, tropoelastin vessels were created by dipping ice scaffolds into dissolved tropoelastin for variable lengths of time (n=3). The resulting vessels were cut into 3 sections longitudinally and viewed under SEM. 4 measurements of wall thickness were taken from each cross-sectional view, at approximately 0°, 90°, 180°, and 270° around the circumference. This resulted in 12 measurements of uniformity for each vessel sample. PCL coated samples (using tropoelastin vessels dipped for <1 sec) were also included. See FIG. 8.

Ice scaffolds may be selectively coated with multiple materials using various methods (FIG. 12). FIG. 12 A demonstrates the addition of three distinct layers of different materials (i-iii). This may be used to replicate the natural blood vessel structure, representing the intima, media, and adventitia. FIG. 12 B demonstrates the selective addition of three distinct layers of different materials. By selectively coating the ice scaffold at different locations, variable functions and wall thicknesses (x, y, and z) can be imparted to the vessel wall. For example, material (i) could be a porous polymer (such as agarose) that is permeable to nutrients and can be used to deliver nutrients, material (ii) could be a biologically derived extracellular matrix component (such as tropoelastin, or collagen) that promotes vascular cell infiltration, and material (iii) could be a synthetic polymer (such as polycaprolactone) that improves mechanical strength for suture retention at an anastomosis. FIG. 12 C demonstrates the selective addition of different materials via different methods to different parts of the ice scaffold. In this example, one material may be painted directly onto the ice scaffold (i), another material may be dip coated directly onto the ice scaffold (ii), another material may be sprayed directly onto the ice scaffold and/or directly onto a prior material coating (iii), and a final material may be dip coated onto any prior material/s (iv). As with FIG. 12 B, application of materials in this way can impart variable functions and wall thicknesses (x, y, and z) to the vessel wall.

After the ice has been coated in the substrate, it is again snap frozen. This step is important particularly where the substrate is provided in the form of a liquid or liquid solution. Immediately after coating, the substrate may still be in liquid form. Snap freezing at this point freezes the substrate coating to lock it into the correct/desired shape. This step also helps to prevent the substrate from melting the ice mold (due to the temperature difference immediately upon coating). Once snap frozen, the substrate-coated ice mold can be safely stored in liquid nitrogen for prolonged periods.

Finally, lyophilisation removed the sacrificial ice mold and the solvents from the substrate coating. The inventors demonstrated the use of ice molds to produce linear vessels of varying diameters and wall thicknesses, bifurcating vessels, multiple bifurcating vessels, and an aortic arch (FIG. 1d). This overall process makes it possible to turn a variety of vascular designs into freestanding vascular structures.

This example reports the use of tropoelastin as a substrate candidate, a protein that is both soluble in water and easily stabilised through heat treatment. This was particularly advantageous as it avoided the use of chemical solvents or cross-linkers that may result in toxic residues. The versatility of this ice system also allowed the molds to be coated with a diverse range of substrates, as well as multiple coatings of different substrates. In particular, demonstrated herein are vessels made using tropoelastin, polycaprolactone (PCL), PDMS, silk, and combinations thereof (FIG. 1e). Having the freedom to utilise combinations of different substrates presented opportunities to tune the vessels for specific mechanical and biological applications.

3D Printing Ice for Engineering Complex Vascular Designs

To improve fabrication of the ice molds, the inventors developed the ability of 3D printing ice molds to create more complex vascular designs at finer resolutions. 3D printing ice directly into the desired mold is advantageous over cast ice molds as it avoids the difficulty of demolding intricate and brittle ice mold designs. To 3D print ice molds, a design was first digitally created and input into a slicer program to optimise the path along which the print-head moves during ice printing (FIG. 4a). This produced a printing script that was then loaded into the 3D printer which carried out the instructions to replicate the original design in ice. The entire 3D printer was placed within a subzero temperature, with water being pneumatically delivered to the print-head from an external reservoir (FIG. 4b). This was necessary to have water delivered to the print-head as a liquid but freeze into ice upon deposition. To prevent condensation damage, the 3D printer controller was placed outside of the subzero environment. The print-head housing includes a commercially available droplet generator with an aluminium housing that was custom designed and machined to allow straightforward integration into the original printer system (FIG. 7). This also housed a micro-dispensing valve that dispensed water in a controlled fashion in order to form ice structures. Thermal regulation of the water was important for controlling the fidelity of the print. Thus, the custom print-head also housed a heating element, providing thermal control of the print-head assembly, which was essential to maintain the water as a liquid during printing.

The resolution of the printed ice features was directly proportional to the quality of the water stream being ejected from the micro-dispensing valve. This parameter was a function of both driving frequency and pneumatic pressure (FIG. 4c). For this example, the inventors found that a minimum pressure of 0.09 atm was required to eject the water from the micro-dispensing valve, and produce a stream of water. However, there were visible differences in the steadiness of the stream whereby there was tendency for the stream to spray at lower frequencies and pressures. This would significantly decrease the fidelity and resolution of the 3D printed ice. To assess the quality of the ejected water, the inventors analysed the consistency of the water droplets ejected by the micro-dispensing valve. The inventors found, for this particular set up, that a minimum driving frequency of 200 Hz produced regularly spaced and sized droplets, although a higher pressure of 0.11 atm and a higher frequency of 400 Hz resulted in improved droplet resolution and consistency. Under ideal conditions, the droplets could be measured to be approximately 0.5 mm in diameter. The skilled address will appreciate that a different set of pressures and frequencies (including no pressure or frequency at all) may be required for a different water ejection system.

By optimising the pressure and driving frequency for the micro-dispensing valve as well as the print-head path of movement during a print, complex and detailed vascular designs could be accurately turned into ice molds. This allowed a reduction in the size of 3D printed ice features to approximately 1 mm in diameter. To demonstrate, the inventors 3D printed ice mold designs in each of the three main basic vascular shapes of bifurcations, networks, and loops, whilst maintaining precision and consistency of the printed features (FIG. 4d).

Ice scaffolds can be fabricated in a configuration that is accompanied by an external scaffold, also made from ice (FIG. 10). In this way, a material may be injected into the cavity between the internal and external scaffold to form a coating. This configuration also allows for an alternative method of varying the wall thickness, depending on the geometry of the internal and/or external scaffolds. In this example, the resulting wall thickness will be tapered between the dimensions of x and y.

Ice scaffolds can be fabricated with additional surface features to enable the fabrication of luminal structures in the casting (FIG. 11). In this example, the ice scaffold is created to contain ribbed features. These cavities will be infiltrated by the material coating and replicate the structure. This can be used to create such features as luminal valves for venous applications.

Modification of a 3D Printer for Printing Water

All 3D printing was performed using a Cocoon Create 3D Printer (Winplus, Australasia) modified with a custom designed print-head to allow automated water deposition. The skilled addressee will appreciate that any modifiable 3D printer could be used. The print-head housed a micro-dispensing valve (Lee Company) used for dispensing pneumatically controlled distilled water. The micro-dispensing valve was controlled by a driver (Lee Company) in conjunction with a square-wave control signal generated by a microcontroller board (Arduino LLC) (FIG. 6).

FIG. 6 is a schematic of the driving electronics for micro-dispensing valve. The electrical circuitry allows either a signal from the 3D printer or a manual override feature to drive an Arduino microprocessor. The Arduino microprocessor subsequently sends a 0 V to +5 V square-wave Control Signal to the valve driver. The square-wave Control Signal determines the frequency at which the valve driver actuates the micro-dispensing valve. To operate the valve, the valve driver operates a spike voltage of +21 V to actuate the valve, but quickly returns to a lower hold voltage of +3.3 V which is enough to maintain the open position of the valve without overheating the valve itself.

The microcontroller board could be operated both manually and automatically. Under manual operation, a momentary switch controlled the microcontroller board to both initiate and terminate a square wave control signal. This control signal was sent to the driver of the micro-valve. Under automated operation, the micro-dispensing valve was able to be switched on or off synchronous with the 3D printer axial movements. The control signals from manual operation overrides the signals from automatic operation.

The custom print-head was designed to minimise the need for modifications to integrate with the 3D printer (FIG. 7). The print-head block was machined out of aluminium, consisting of two through-holes, housing the thermal-sensor and heating element, and a central threaded through-hole that houses the micro-dispensing valve. This design allowed the print-head to house the stock heating element and temperature sensor to provide thermal control. A water delivery tube acted as a water transporter between the heated print-head and the water reservoir located externally to the subzero ambient environment. The 3D printer, including its modifications, was placed into a freezer (SANYO) which provided the necessary ambient temperature of −30° C. for ejected water to freeze into ice upon deposition. The water in the delivery tube inside the subzero ambient environment was maintained above freezing temperature using a combination of insulation and a rope heater (Omega Engineering Inc.) coupled to a thermostat. To avoid the potentially harmful effects of condensation, the power supply and printer control unit were placed outside of the subzero environment.

Design and Fabrication of Hierarchical Vascular Structures 3D printing ice also presented an opportunity to create ice molds for a broad range of vascular designs. For complex vascular structures, however, hierarchical dimensions must be considered in order to have valid fluid flow. One of the biggest advantages of the increased resolution through 3D printing is to also have finer control over the dimensions of the vessel, allowing the inventors to fabricate true hierarchical vascular structures. To the best of the inventors' knowledge, this is novel as it utilized design parameters, such as Murray's Law, as part of the process for engineering complex freestanding vascular structures using biological materials. As a proof of concept, the inventors focussed on introducing hierarchically dimensioned branches in vascular bifurcations, networks, and loops.

In the first instance the inventors introduced hierarchical dimensioning to bifurcating vascular structures (FIG. 5a). The diameter of the parent branch was 3D printed to be larger than the bifurcated daughter branches, so as to facilitate mass conservation and sustain non-turbulent fluid flow. The ideal relationship between these diameters has been previously defined by Murray's Law, which correlates the dimensions of bifurcated daughter branches to the parent branch for a lumen-based system. The inventors confirmed that the relationship between the parent branch and daughter branch along each bifurcation in the hierarchy was consistent with the theory as described by Murray's Law (FIG. 5a).

To increase the complexity, hierarchical dimensioning was introduced into a vascular network design. In this context, the vascular network was defined as a design which includes multiple levels in its bifurcating hierarchy (FIG. 5b). The 3D printed ice mold was also validated by Murray's Law to contain parent and daughter branches that follow the theoretical relationship (FIG. 5b). This vascular network design additionally illustrated the lower limit of the 3D printing system to be approximately 1 mm diameter branches. This limit is determined by the current hardware and will improve with further optimisation and upgrades to the system. The current system does not impose such limitations to the upper limit on printable hierarchical networks. Therefore, it is possible to 3D print ice molds for hierarchical vascular networks with a range of diameters.

Finally the inventors progressed to introducing hierarchical dimensioning to a vascular loop design. In this context, a vascular loop was defined as a design that bifurcated to smaller diameter branches in the hierarchy, but also converged back to larger diameter branches within the same structure (FIG. 5c). In this 3D printed mold, the relationship between parent and daughter branches was validated by Murray's Law along both bifurcating and converging branches along the hierarchy (FIG. 5c). The ability to 3D print ice molds for hierarchical vascular loops is a conceptual precursor for fabricating vascular bed structures for supporting synthetic tissue growth in vitro.

Next, the ice molds for the hierarchical vascular bifurcations, networks, and loops were dip coated in silk to form freestanding vascular structures (FIG. 5d-f). These vascular structures were subsequently proven to be perfusable to liquid flow (FIG. 5g-i). Collectively, these steps were a demonstration of the simplicity of designing, coating, and implementing effective hierarchical vascular designs.

3D printing ice molds for more intricate and complex vasculature provides great potential for designing vascular structures for a specific purpose. These can range from the replacement of a damaged bifurcating vessel in a patient, to an entire hierarchical vascular network system for supporting synthetic tissue growth. For these applications, this fabrication method has the ability to replicate biological vasculature as well as design synthetic vascular systems. The latter requires considerations of the mechanical effects of fluid flow, especially at regions of bifurcation.

FIG. 9 demonstrates the ability to fabricate ice scaffolds that are freestanding and can branch into space. The hierarchical dimensioning is preserved during the fabrication process, as exemplified with three hierarchical tiers (labelled A, B and C respectively). Level A branches have a diameter of 4 mm, level B branches have a diameter of 3.17 mm, and level C branches have a diameter of 2.5 mm.

Physical and Mechanical Properties

The fabricated vessels were then subjected to a series of physical and mechanical tests to validate their suitability for grafting. Examination under scanning electron microscopy (SEM) revealed that tropoelastin vessels possessed a porous luminal surface with pores that were less than 10 µm in diameter (FIG. 2a). These pores were connected to the substructure within the vessel walls (FIG. 2a-zoomed). The cross-section of the tropoelastin vessels revealed channels that were radially connected between the luminal and extra-luminal surfaces (FIG. 2b). These channels were approximately 2 µm in width (FIG. 2b-zoomed) allows diffusion between the luminal and extra-luminal surfaces. Due to the uniform and regular structures in the cross-sectional vessel wall, the tropoelastin vessels were considered to be transversely isotropic such that the mechanical properties in the circumferential and longitudinal directions were equivalent. The extra-luminal surface was also porous (FIG. 2c) although the size of the pores was much smaller than those observed on the luminal surface. Similar to the luminal surface, the pores on the extra-luminal surface were also connected to the substructure within the vessel walls (FIG. 2c-zoomed). Collectively, the permeability between the luminal and extra-luminal surfaces indicated potential functionality in the diffusion of nutrients between the luminal and extra-luminal space.

The inventors next subjected the tropoelastin vessels to cyclic tensile testing at a 50 mm/min strain rate with 15% extension. The resulting cyclic stress-strain curves were similar in shape and magnitude, demonstrating consistent mechanical behaviour of the material in the range of strain conditions typical of physiological contexts (FIG. 2d). Hysteresis was evident from the cyclic stress-strain curves with a calculated energy loss of 76.60±1.40% throughout the entire 500 cycles for all samples tested (FIG. 2e). Although there is limited information regarding the exact energy loss in human blood vessels, the calculated energy loss of the tropoelastin vessels is relatively high compared to the literature range for blood vessels of 15-20%. This discrepancy, however, may be attributed to the lack of smooth musculature and collagen in the tropoelastin vessels. As such, the inventors expect that cell recruitment and subsequent remodelling post implantation would result in the addition of both components so that energy losses may be improved over time in situ. Despite this energy loss, the superimposed stress-strain cycles indicated no plastic deformation to the vessel under testing conditions.

The loading phase of the cyclic stress-strain graph for tropoelastin vessels reflected a biphasic mechanical behaviour, whereby the stiffness was initially higher but decreased during the second phase, and the compliance was initially lower but increased over the second phase (FIG. 2d). The point at which stiffness and compliance changed was termed the critical stress. With respect to burst pressure, this behaviour indicated that the tropoelastin vessel supported pressure increases with small deformations up until the critical stress, after which small increases in pressure would result in large deformations. The critical stress, therefore, effectively defined the burst pressure of the vessel. For tropoelastin vessels, this burst pressure was not adequate for sustaining arterial blood pressure. The inventors, therefore, additionally coated the tropoelastin vessels with polycaprolactone (PCL), a commonly used and FDA approved biomaterial. Compared to the burst pressure of 21.23±0.71 mmHg for tropoelastin vessels without PCL, tropoelastin coated with PCL achieved a burst pressure of 1128.33±68.82 mmHg. This improved burst pressure was closer to that of the human saphenous vein (1599±877 mmHg) (FIG. 2f), which is a current benchmark standard for autologous vascular grafting. That the tropoelastin/PCL vessels would withstand supraphysiological blood pressures upon initial surgical implantation indicated favourable conditions for immediate post-operative success in grafting applications.

The addition of PCL to tropoelastin vessels also significantly increased the Young's Modulus, compared to tropoelastin vessels without PCL. This increase was dependent on the number of layers of additional PCL, with more PCL layers significantly improving the Young's Modulus. In particular, 5 layers of PCL resulted in a Young's Modulus that was comparable to the circumferential and longitudinal moduli of the saphenous vein (FIG. 2g). Similarly, ultimate tensile strength (UTS) also improved with the addition of PCL. The addition of at least 3 layers of PCL was needed for a significant improvement compared to tropoelastin vessels without PCL (FIG. 2h). The addition of 5 layers of PCL resulted in an UTS that was closer to the circumferential ultimate tensile strength of the saphenous vein (1.8±0.8 MPa).

Suture retention strength also significantly improved through the addition of PCL to tropoelastin vessels, in a layer dependent manner, compared to tropoelastin without PCL (FIG. 2h). An additive relationship was observed when comparing the suture retention strengths of tropoelastin without PCL, 3 layers of PCL without tropoelastin, and tropoelastin with 3 layers of PCL. This indicated that the suture retention strength of tropoelastin/PCL vessels was the sum of the suture strength of tropoelastin and PCL separately. This further suggested that the mechanical properties can be modularised through combining different materials. The suture retention strength of tropoelastin/PCL vessels was stronger compared to rat abdominal aorta and that of human saphenous veins (196±2 gf).

Characteristics for Biological Integration

Next the performance of the fabricated blood vessels was investigated from a biological perspective. The degradation of tropoelastin vessels in 100% foetal bovine serum (FBS), which simulated in vivo conditions, was assessed relative to phosphate-buffered solution (PBS) as a baseline control. The tropoelastin vessels were able to retain physical integrity even after 14 days as they maintained their tubular shape (FIG. 3a). The mass retention of tropoelastin vessels after the first 6 hours was 95.56±6.49% when incubated in PBS, which was comparable to vessels that were incubated in 100% FBS with a mass retention at 96.99±2.19% (FIG. 3b). The relatively fast, and comparably similar, initial mass loss within the first 6 hours may have resulted from non-stabilised protein that was shed by the vessels upon immersion in liquid media. By the end of day 14, the mass retention of tropoelastin vessels that were incubated in PBS did not significantly change and remained at 93.61±1.59%. Tropoelastin vessels incubated in 100% FBS demonstrated significant mass loss up until day 3, resulting in a mass retention of 77.77±7.71%. However, there was no further significant mass loss after day 3 with the retained mass remaining constant until the end of day 14. This suggested that the vessels had stabilized. The inventors did not assess tropoelastin/PCL vessels because PCL is known to degrade relatively slowly.

The inventors next assessed glucose diffusion across the tropoelastin vessel walls. By measuring the passive diffusion of glucose between the luminal and extra-luminal space of tropoelastin vessels (FIG. 3c), the inventors validated its potential for supporting synthetic tissue viability. The diffusion rate of glucose through the tropoelastin vessels was measured to be 0.384±0.088 mmol/m$^2$/min which was comparable to whole body glucose uptake of 0.4-2.1 mmol/m$^2$/min (normalised to body tissue area). However, it should be noted that the same area of bodily tissue would typically have a higher area of vascular tissue due to the amount of capillaries and micro-vasculature that are present. Thus it can be inferred that the glucose diffusion rate in whole body tissue would decrease once normalised against the corresponding area of vascular tissue, becoming more directly comparable to the measured glucose diffusion rate of tropoelastin vessels.

The inventors also evaluated the biocompatibility of the tropoelastin vessels. Samples of the tropoelastin vessels were seeded with human umbilical vein endothelial cells (HUVECs) and cultured for up to 1 week to assess its ability to support cellular adhesion and proliferation. Over the course of 7 days, there was a significant fold change in the cellular DNA content, indicating the tropoelastin vessels supported HUVEC proliferation over this time period (FIG. 3d). Confocal microscopy images further validated cellular adhesion and proliferation, showing that HUVECs formed a monolayer over the course of 7 days whilst maintaining the correct cobblestone appearance (FIG. 3e). 3D z-stack images confirmed that the cells formed a characteristic monolayer (FIG. 3f), which is also the expected outcome for in vivo endothelialization.

The tropoelastin vessels were also stimulated in a modelled physiological environment by incorporating the vessels onto a modified Langendorff Perfusion system. An introduced pulsatile flow elicited observations of the tropoelastin dilating and contracting back to its original physical shape, indicating no plastic deformation of the vessel (FIG. 3g).

It will be understood that the invention disclosed and defined in this specification extends to all alternative combinations of two or more of the individual features mentioned or evident from the text or drawings. All of these different combinations constitute various alternative aspects of the invention.

The invention claimed is:

1. A method of fabricating a cast biomaterial with internal hierarchical structure, the method comprising:
    coating a biomaterial onto at least a portion of an external surface of a sacrificial mold having a hierarchical structure, wherein the sacrificial mold is a sacrificial ice mold, and forming a casting of the biomaterial on the sacrificial ice mold, the casting having an internal hierarchical structure corresponding to the external surface of the sacrificial ice mold; and
    subjecting the sacrificial ice mold and the casting to a temperature and pressure to lyophilise the sacrificial ice mold from the casting to form the cast biomaterial with internal hierarchical structure.

2. The method of claim 1, wherein prior to the step of applying a biomaterial to the sacrificial ice mold, the method further includes forming the sacrificial ice mold by a method selected from: sculpting or machining the sacrificial ice mold from a solid sacrificial mold material; or casting or 3D printing water and solidifying the water to form the sacrificial ice mold.

3. The method of claim 2, wherein the step of forming the sacrificial ice mold includes 3D printing water.

4. The method of claim 1, wherein the step of coating the biomaterial onto the sacrificial ice mold to form the casting of the biomaterial on the external surface of the sacrificial ice mold includes forming a layer of the biomaterial with a layer thickness of 10 mm or less.

5. The method of claim 1, wherein, after the step of lyophilizing the sacrificial ice mold from the biomaterial, the method further includes applying one or more coating layers to at least one surface of the cast article, and forming a coated and/or multilayered cast article.

6. The method of claim 1, wherein the biomaterial is applied to the external surface of the sacrificial ice mold by dip coating the sacrificial ice mold into the biomaterial or spray coating the biomaterial onto the external surface of the sacrificial ice mold.

7. The method of claim 1, wherein the hierarchical structure includes one or more branches with a cross-sectional area corresponding to a diameter of 50 mm or less.

8. The method of claim 1, wherein prior to the step of coating a biomaterial onto at least a portion of the external surface of the sacrificial ice mold, the method further includes forming the sacrificial ice mold by 3D printing water to form the sacrificial ice mold.

9. The method of claim 1, wherein the hierarchical structure includes at least a parent vessel and a plurality of daughter vessels extending from a terminal end of the parent vessel, and wherein the parent vessel and the plurality of daughter vessels are sized such that the hierarchical structure obeys Murray's law.

10. The method of claim 1, wherein the step of coating the biomaterial onto the sacrificial ice mold includes forming a tubular layer of the biomaterial around a tubular receiving surface of the sacrificial ice mold.

11. The method of claim 1, wherein prior to the step of lyophilizing the sacrificial ice mold from the biomaterial, the method further includes applying one or more coating layers to at least one surface of the casting, and forming a coated and/or multilayered casting.

* * * * *